US 6,551,298 B1

(54) CONTROLLED MEDICAMENT SECURITY ENCLOSURE SYSTEM

(76) Inventors: Jack Y. Zhang, 1886 Santa Anita Ave., South El Monte, CA (US) 91733; Frank Zhishi Xia, 1886 Santa Anita Ave., So. El Monte, CA (US) 91733; Mary Ziping Luo, 1886 Santa Anita Ave., So. El Monte, CA (US) 91733

( * ) Notice: Subject to any disclaimer, the term of this patent is extended or adjusted under 35 U.S.C. 154(b) by 136 days.

(21) Appl. No.: 09/718,112

(22) Filed: Nov. 21, 2000

(51) Int. Cl.[7] .......................... A61B 19/00; B65D 83/14
(52) U.S. Cl. .................. 604/403; 206/363; 604/91; 604/259; 604/162
(58) Field of Search ................ 604/162, 5.01, 604/403, 430, 259, 91; 206/362, 363, 364, 366, 15.3; 417/474

(56) References Cited

U.S. PATENT DOCUMENTS

| | | | | |
|---|---|---|---|---|
| 880,679 A | * | 3/1908 | Mason | |
| 1,625,035 A | * | 4/1927 | Lilly | |
| 1,858,146 A | * | 5/1932 | Ferguson | |
| 3,719,213 A | * | 3/1973 | Quick | 141/5 |
| 4,351,335 A | * | 9/1982 | Whitney et al. | 128/218 A |
| 4,467,947 A | * | 8/1984 | Minneman | 224/253 |
| 4,813,937 A | * | 3/1989 | Vaillancourt | 604/131 |
| 4,867,743 A | * | 9/1989 | Vaillancourt | 604/135 |
| 4,979,616 A | * | 12/1990 | Clanton | 206/364 |
| 5,024,326 A | * | 6/1991 | Sandel et al. | 260/366 |
| 5,289,858 A | * | 3/1994 | Grabenkort | 141/97 |
| 5,324,258 A | * | 6/1994 | Rohrbough | 604/86 |
| 5,533,994 A | * | 7/1996 | Meyer | 604/416 |
| 5,549,651 A | * | 8/1996 | Lynn | 604/283 |
| 5,620,420 A | * | 4/1997 | Kriesel | 604/133 |
| 5,647,845 A | * | 7/1997 | Haber et al. | 604/32 |
| 5,924,562 A | * | 7/1999 | Barth | 206/63.5 |
| 5,947,951 A | * | 9/1999 | Ortiz et al. | 604/403 |
| 6,067,909 A | * | 5/2000 | Knoster, Jr. | 102/517 |
| 6,149,623 A | * | 11/2000 | Reynolds | 604/82 |
| 6,325,116 B1 | * | 12/2001 | Savage et al. | 141/349 |

* cited by examiner

*Primary Examiner*—Ira S. Lazarus
*Assistant Examiner*—Tu Cam Nguyen
(74) *Attorney, Agent, or Firm*—Albert O. Cota

(57) ABSTRACT

A controlled medicament security enclosure system that houses liquid filled reservoirs which consists of a portable enclosure (20) formed with a top half (22) and a bottom half (24) that permanently snap together to form a secure inseparable repository for the reservoirs. Inside the enclosure is at least one glass vial (36) for storing the liquid medicament with each vial having a sliding piston stopper (42) within that seals the inside of the vial and slides to maintain the liquid air free regardless of the volume. An adapter socket (48) is removably attached to the stopper and includes a hollow needle that pierces the stopper and permits a flow-path for the liquid. A flexible outlet tube (62) along with connectors on each end transmit the medicament to a mechanical drug delivery system that has a peristaltic pump and a control module.

20 Claims, 4 Drawing Sheets

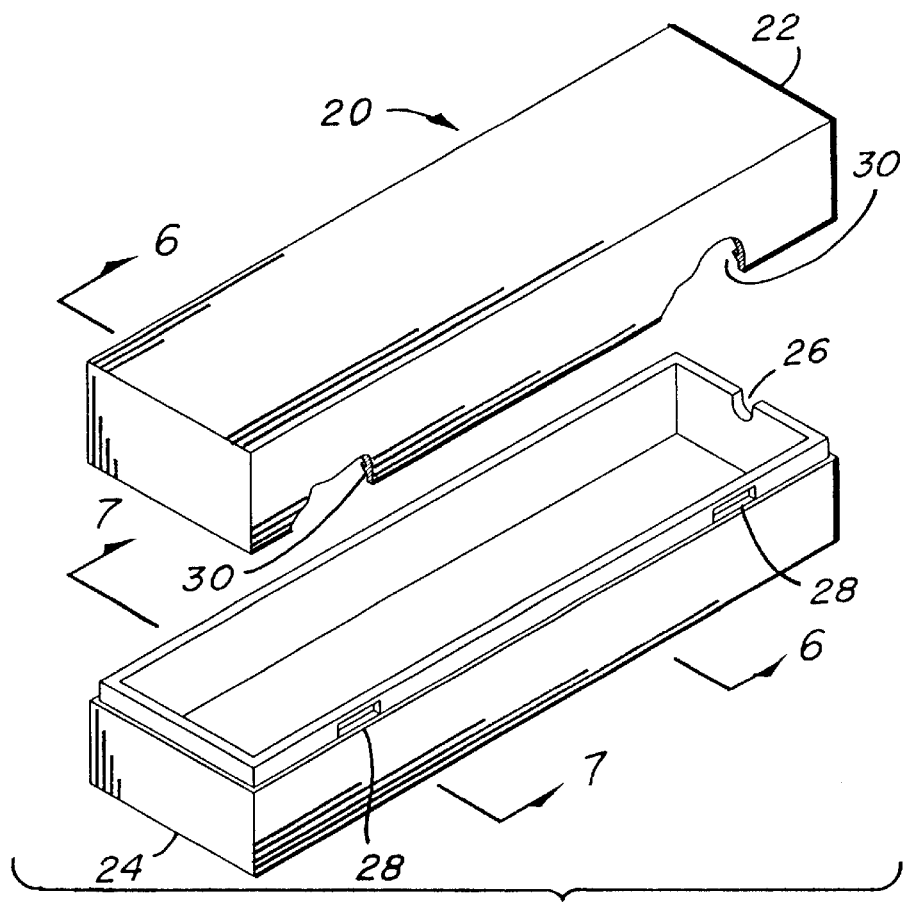
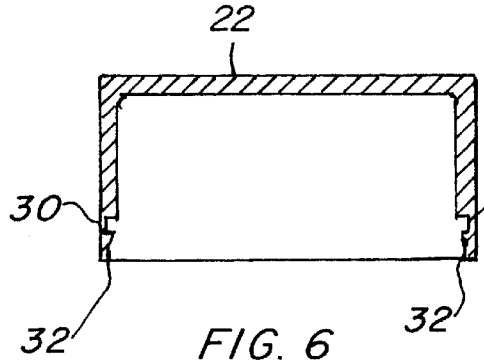
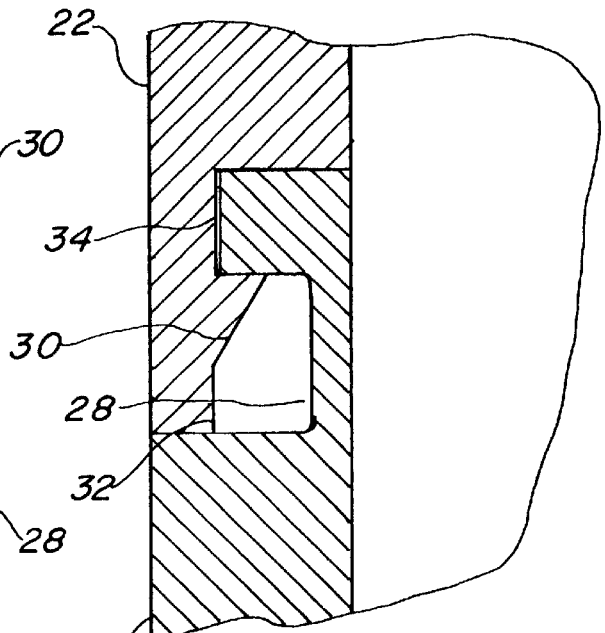

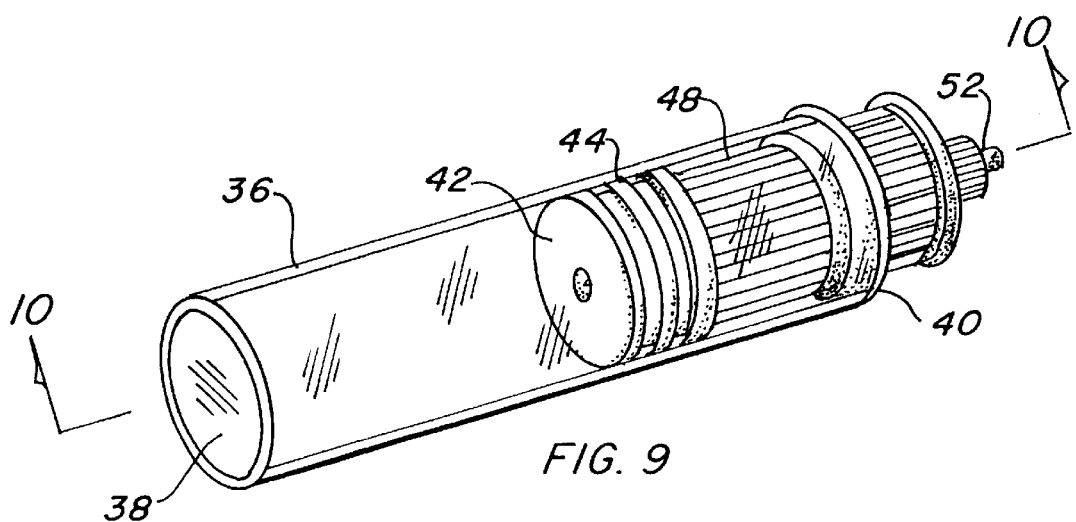
FIG. 9
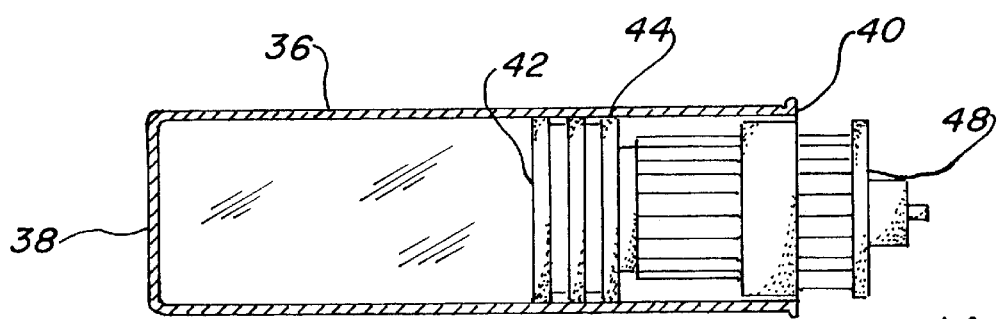
FIG. 10
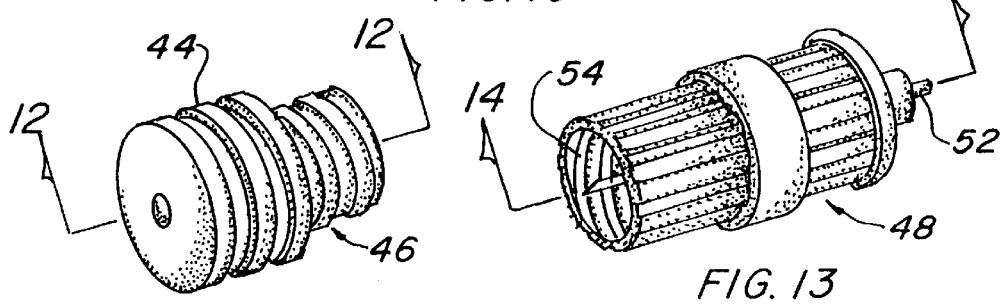
FIG. 11
FIG. 13
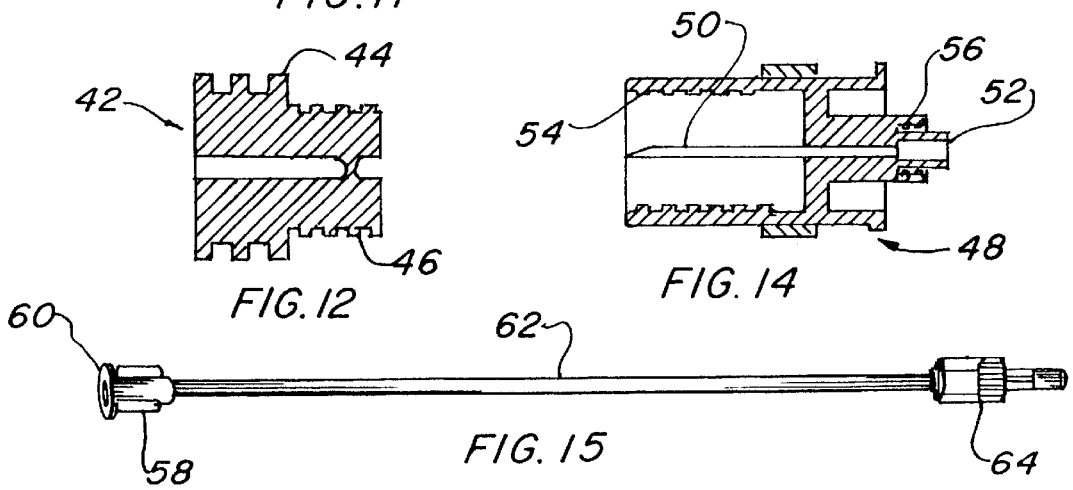
FIG. 12
FIG. 14
FIG. 15

CONTROLLED MEDICAMENT SECURITY ENCLOSURE SYSTEM

TECHNICAL FIELD

The invention pertains to drug delivery systems in general and more particularly to a controlled medicament enclosure system that is secured by permanently sealing a two piece enclosure, which contains medicament vials, by snapping two halves of the enclosure together.

BACKGROUND ART

Previously, many types of reservoir modules have been used in endeavoring to provide an effective means for enclosing and protecting medicament containing vials. Some systems employ plastic global containers or even plastic bags for containment and distribution of medicinal agents.

A search of the prior art did not disclose any patents that possess the novelty of the instant invention, however the following U.S. patents are considered related:

| U.S. Pat. No. | Inventor | Issue Date |
| --- | --- | --- |
| 5,324,258 | Rohrbough | Jun. 28, 1994 |
| 5,060,812 | Ogle, II | Oct. 29, 1991 |
| 4,657,486 | Stempfile et al. | Apr. 14, 1987 |
| 4,259,956 | Ogle | Apr. 7, 1981 |

Rohrbough in U.S. Pat. No. 5,324,258 teaches a medicament reservoir module for attachment to a pumping and control module which incorporates a conventional vial that is sealed at an open end with a penetrable stopper. A hollow needle is attached to an adapter that releasibly connects the stopper and pierces the stopper, thus providing a medicament flow path through a slack length of flexible tubing. The tubing attaches to a peristaltic pump in a pumping and control module. A housing supports the vial, encloses the adapter, hollow needle, and slack tubing, and releasibly connects to the pumping and control module, thereby providing a detachable reservoir module.

U.S. Pat. No. 5,060,812 issued to Ogle, H is for a medication container stopper which has a elastomeric plug forming a friction fit in an opening of a container. A first cavity in an exterior surface of the plug opens and diverges away from an interior surface of the plug. A second cavity similarly opens and diverges away from the exterior surface of the plug. The bottom of the cavities have an elongated groove with a bottom which defines one face of a diaphragm which is of a thickness that permits the diaphragm to be ruptured by inserting a conventional hypodermic syringe nozzle into the cavity in the exterior surface of the plug.

Stempfile, et al. in U.S. Pat. No. 4,657,486 discloses a portable infusion device for injecting medicinal fluids into human or animal bodies by means of a positive pressure pump that is automatically operated at selected time intervals to inject accurate amounts of fluid medicine into the body.

Ogle in U.S. Pat. No. 4,259,956 teaches a medicament package having a shell vial with an open end. An imperforate resilient stopper seals a closed end of the vial, and a peripheral portion of the stopper facing the open end prevents the outward movement of the stopper within the vial. The stopper is adapted to reciprocate in a piston-like fashion though the closed end of the vial to expel the contents through a hollow needle when punctured thorough the stopper.

DISCLOSURE OF THE INVENTION

In the past, controlled injectables have been housed in a variety of containers which include a sterile reservoir for connection directly to an ambulatory infusion pump, also referred to as a peristaltic pump, using hooked brackets for attachment. Other devices are enclosed in housings that are removably attached to the pumping apparatus and use vials that are replaceable and mount into the housing. Still other approaches to the storage of medicament in a packaged arrangement is to use a flexible bag which decreases in size as the liquid within is dissipated by the negative pressure created by the peristaltic pump.

The primary object of the invention is to provide a security box or enclosure that is safe to handle and easy to use as the construction of the enclosure is such that two halves are formed, and when one or more medicament vials are positioned therein, with tubing projecting from one end, the halves are snapped together and form a permanent juncture, thus protecting the sterile material for a single use.

An important object of the invention is that it is easy to use. When the vials are filled with the liquid medicament and the tubing is attached, they are simply placed inside the bottom half of the security enclosure. The top half of the enclosure is then positioned above, thereby permitting them to mate easily, and when compressed together they permanently snap in place to form a positive closure with no further handling necessary.

Another object of the invention is its convenience, as the device is smaller in size then conventional enclosures and for portable drug delivery systems it is considerably easier to carry since it is flat and has no outside projections.

Still another object of the invention is that a short hollow needle is utilized in the vial that is less than 2 inches (5.08 cm) long which has an advantage over the prior art that requires a much longer needle with its accompanying difficulties.

Yet another object of the invention is its adaptability, as more than one vial may be packaged in the enclosure by simply adding a partition and using multiple vials that are attached together on the outside with flexible tubing.

A further object of the invention is directed to a much longer shelf life of the medicament when it is stored in a glass vial. For example, if the medication is morphine the shelf life is from 7 to 10 days in plastic bags even if refrigerated. In glass vials the medication shelf life is extended to 18 months or longer.

A significant object of the invention is that the enclosure can be made in a rectangular shape, an enclosure having a top half with rounded edges or an enclosure with all edges rounded. In particular, the rectangular shaped enclosure allows multiple enclosures to be easily stacked together when packaged in a shipping container.

A final object of the invention is directed to its ability to be easily produced in a formal government approved Current Good Manufacturing Practice facility, as it meets or exceeds the requirements of Federal Code 21 CFR chapter 1, supervised by the Federal Food and Drug Administration.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 5 is a partial exploded and cut away view of the preferred embodiment.

FIG. 6 is a cross-sectional view taken along lines 6—6 of FIG. 5.

FIG. 7 is a cross-sectional view taken along lines 7—7 of FIG. 5.

FIG. 8 is a partial cross-sectional view of the junction of the top and bottom half of the enclosure mated together with one of the jaws snapped into one of the recesses.

FIG. 9 is a partial isometric view of the medicament vial completely removed from the invention for clarity.

FIG. 10 is a cross-sectional view taken along lines 10—10 of FIG. 9.

FIG. 11 is a partial isometric view of a sliding piston stopper completely removed from the invention for clarity.

FIG. 12 is a cross-sectional view taken along lines 12—12 of FIG. 11.

FIG. 13 is a partial isometric view of an adapter socket completely removed from the invention for clarity.

FIG. 14 is a cross-sectional view taken along lines 14—14 of FIG. 13.

FIG. 15 is a partial isometric view of a flexible outlet tube completely removed from the invention for clarity.

BEST MODE FOR CARRYING OUT THE INVENTION

Figure 1:
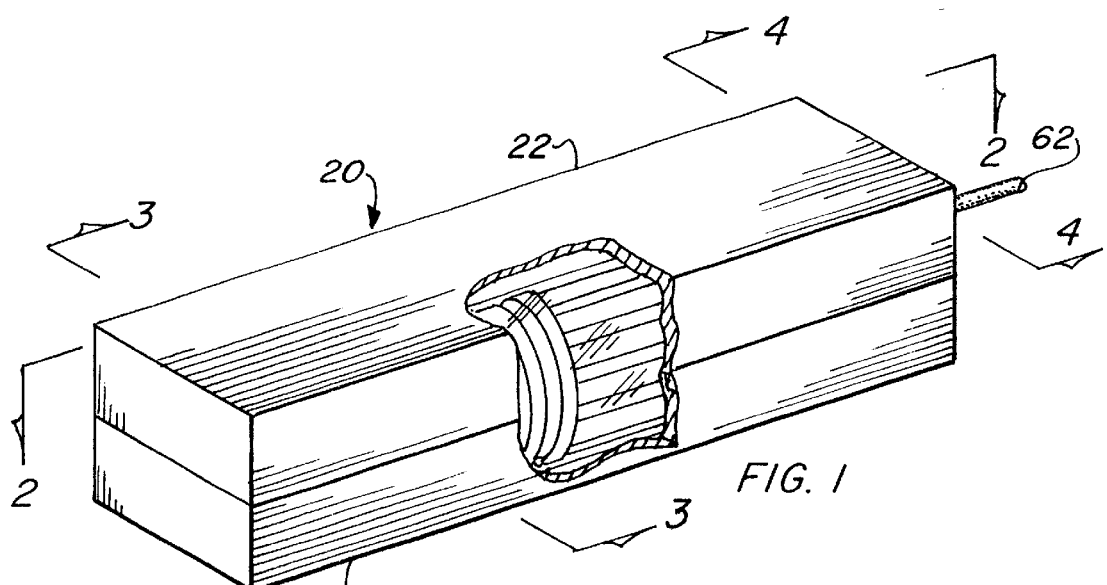
FIG. 1 is a partial isometric view of the preferred embodiment

The best mode for carrying out the invention is presented in terms of a preferred embodiment and a second embodiment. Both embodiments are basically the same except the second embodiment utilizes multiple medicament vials in the enclosure. The preferred embodiment is shown in FIGS. 1 thorough 15, and is comprised of a portable enclosure 20 of a configuration to accept one or more medicament reservoirs. The enclosure is configured with a top half 22 and a bottom half 24 formed in such a way that they permanently snap together to form a secure, inseparable repository for the reservoirs. The portable enclosure 20 is generally rectangular in configuration and of a size in its interior to loosely accommodate reservoirs. The enclosure's top half 22 and bottom half 24 each have a mating arched opening 26 that jointly creates a round opening for outlet tube egress. The portable enclosure 20 has a plurality of notched recesses 28 in the top half 22, and the bottom half 24 includes a plurality of mating tapered jaws 30, as shown in FIGS. 3 through 8, such that the jaws 30 are urged outward when the halves 22, 24 are pressed together, thus permitting the jaws 30 to snap into the recesses 28 which forms a non-removable junction once they are combined.

Further, the same mating edges of the top and bottom 22, 24 contain an interface joint comprising an internal indentation 32 on the top and an opposed inward recessed step 34 on the bottom, as illustrated best in FIG. 8, both continuing around each interfacing periphery. The indentation 32 and step 34 are sized to mate together in a slip fit such that there is structural integrity of the joint when they are snapped together, with the recesses 28 and jaws 30 providing the purchase for the tension union. Alignment is assured by the indentation 32 and step joint. It should be noted that the top and bottom configuration may be reversed as this relationship is of little consequence in the structural configuration of the enclosure. Further, the length of the recesses 28 and jaws 30 are illustrated in the drawings as being in four separate locations and are relatively short in respect to the overall length of the enclosure 20. However, this is only representative, as the recesses 28 and jaws 30 may be any length including extending around the entire perimeter. Since the enclosure halves 22 and 24 are permanently secured, the complete enclosure is disposable after the first usage which insures the sterility of the system.

Both halves of the enclosure 20, are preferably constructed of a thermoplastic material such as polyethylene, polystyrene, polypropylene, polycarbonate, polyester, polyvinylchloride, polysulfone, polyurethane, cellulose or other equivalent polymers. The material may be transparent, translucent or opaque and still provide the requisite utility.

At least one glass medicament vial 36, defined generally as a reservoir, is disposed within the enclosure 20 and contains the liquid medicament therein. This medication is typically morphine, hydromorphine, meperidine or the like, however, almost any medication that is administered intravenously may be utilized within the vial 36. The vial 36, as illustrated by itself, away from the container 20 in FIGS. 9 and 10, is tubular in shape and has straight walls, closed on a first end 38 and open on a opposed second end 40. This type of glass vial 36 is well known in the art and has been used for many years for this purpose and is still currently available on today's market. The vial 36 is illustrated best in FIGS. 9 and 10, and may have a small lip around the second open end 40, however, this feature is not necessary for its function.

A sliding piston stopper 42 is compressed within the vial 36 and contiguously engages the medicament. With the arrangement, the stopper 42 is free to slide within the vial confines in a hermetically sealed manner when medicament is transferred through the peristaltic pump in the drug delivery system. The stopper 42 is shown by itself in FIGS. 11–12 and is formed of a resilient thermoplastic material with a plurality of compressible, peripheral chevrons 44 which seal to the vial 36. Three chevrons 44 are illustrated, however, any number may be used with equal ease and sealing capability. Integrally-formed stopper attachment means are in the form of stopper external threads 46, which are located on an end opposite the chevrons 44 and are illustrated best in FIGS. 11 and 12. The stopper external threads 46 are preferably of the ACME type, as they are designed for linear action not specifically for sealing and are robust enough for use with the resilient thermoplastic material.

An adapter socket 48 is connected to the stopper 42 and includes a hollow needle 50 on the inside and a fluid outlet 52 on an end opposite the needle. The socket 48 has integrally-formed, adapter socket attachment means in the form of adapter internal threads 54, also of the ACME type, that interface with the stopper external threads 46. When the socket 48 is threaded to the stopper 42, the needle 50 penetrates the stopper 42 such that the needle is in communication with the medicament and the fluid outlet 52. Further, a set of socket outlet internal threads 56 surround the fluid outlet 52. It should be noted that the configuration of the adapter socket 48 permits the hollow needle 50 to be less that 2 inches (5.08 cm) in length which is advantageous as longer needles have a tendency to misalign when penetrating the stopper 42. Also note that the diameter of the adapter socket 48 should be less than the internal diameter of vial 36.

A first tubing connector 58 is attached to the adapter socket fluid outlet 52 for fluid connection to the adapter socket 48. The first tubing connector 58 has external threads 60 that interface with the adapter's socket outlet internal threads 56 in a conventional manner.

A flexible outlet tube 62 is attached to the first tubing connector 58 for transferring medicament from the vial and is a resilient hollow intravenous tube well known in the art. It has been found that an outer diameter of 0.135 inches (0.343 cm) is ideal for the application, however, any common size may be used with equal ease. The free length of the flexible outlet tube 62 should be longer than the length of the vial 36.

A second outlet tubing connector 64 is attached to the flexible outlet tube 62 for interfacing with and delivering medicament to a conventional drug delivery device that includes a pumping and control mechanism. The second outlet tubing connector 64 may be any type, however, the type known by its registered trademark as a LUER LOCK is preferred.

Figure 16:
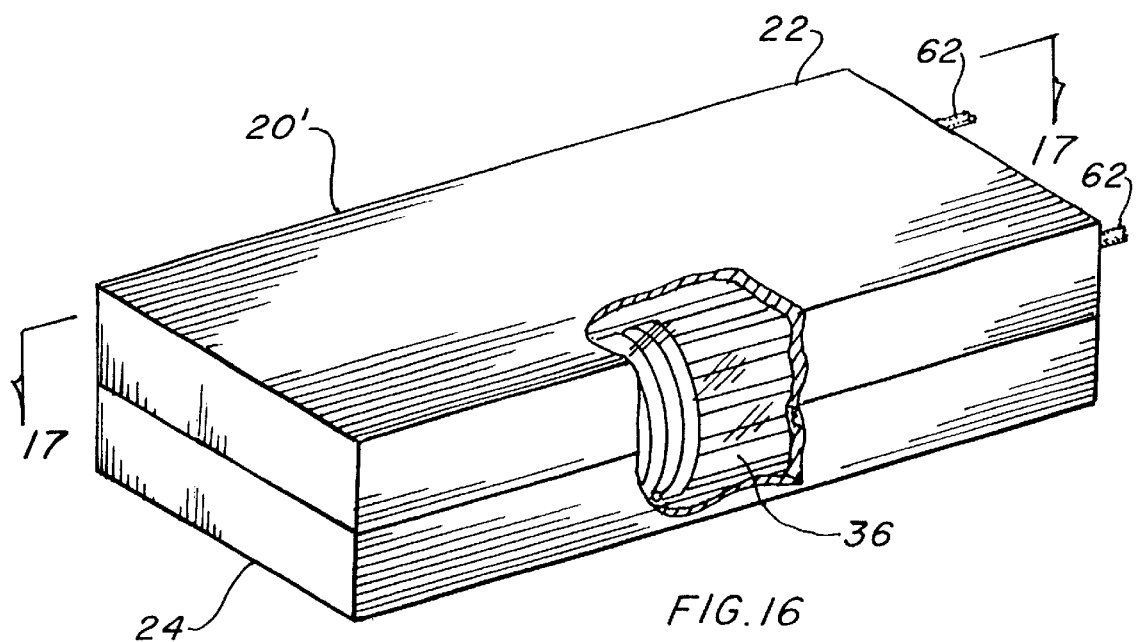
FIG. 16 is a partial isometric view of the second embodiment
Figure 17:
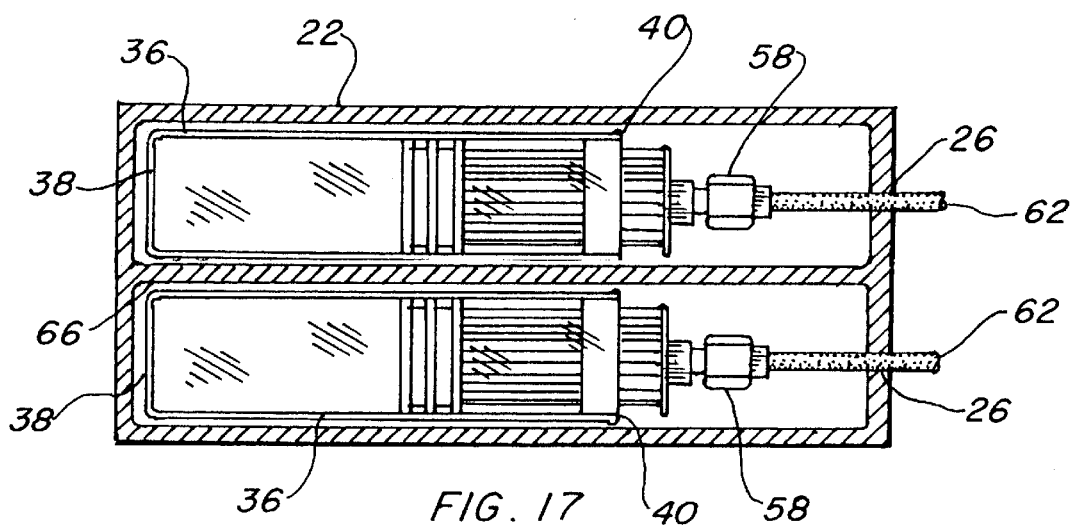
FIG. 17 is a cross-sectional view taken along lines 17—17 of FIG. 16.
Figure 18:
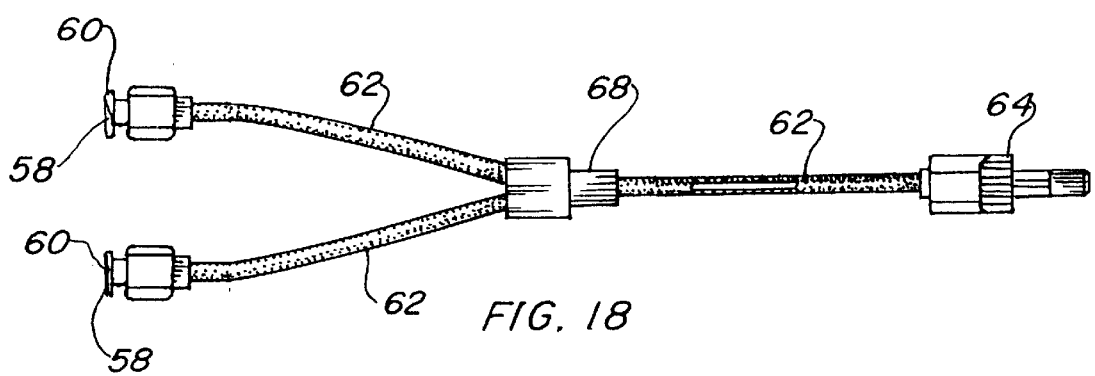
FIG. 18 is a partial isometric view of the flexible outlet tube of the second embodiment having a Y fitting attached for connecting two vials together with the fitting completely removed from the invention for clarity.

The second embodiment is illustrated in FIGS. 16–18 and differs only in the fact that the enclosure 20' is double in width to accommodate two vials 36. A partition barrier 66 is added within the enclosure to separate the vials 36 and could be further duplicated when more than two vials are housed within. As a matter of fact any number of assembled vials 36 may be used in conjunction with the enclosure 20 and as such are presently anticipated. When more than one vial assembly is used, at least one Y fitting 68 is attached within each outlet tube 62 connecting them together and permitting them to join into the remainder of the tube 62 and be attached to the second outlet tube connector 64 thus manifolding them together into a single outlet termination.

Figure 2:
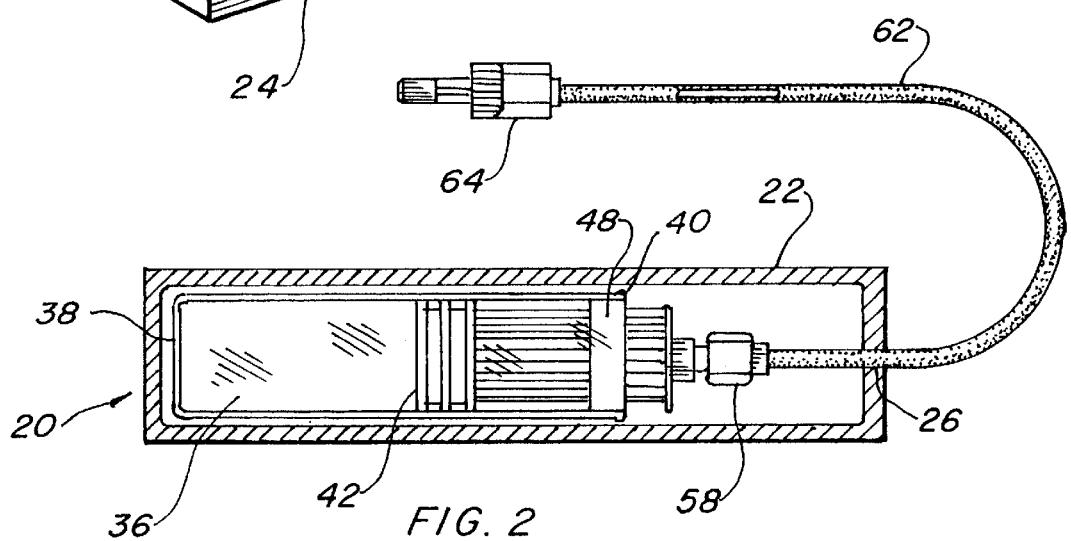
FIG. 2 is a cross-sectional view taken along lines 2—2 of FIG. 1.
Figures 3, 4:
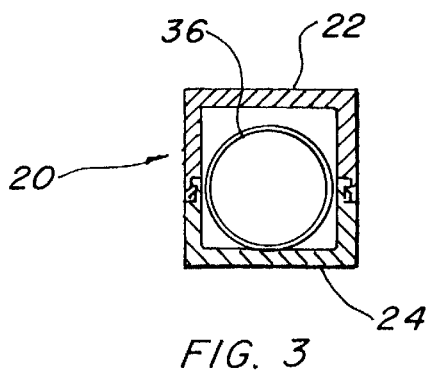
FIG. 3 is a cross-sectional view taken along lines 3—3 of FIG. 1.
FIG. 4 is a cross-sectional view taken along lines 4—4 of FIG. 1.

In basic use, the piston stopper 42 is inserted into the vial 36 along with its attached adapter socket 48. The tubing 62 along with its attached connectors 58 and 64 and the liquid medicament is inserted under pressure which causes the stopper 42 to slide toward the open second end 40 as shown in FIG. 2. This assembly is accomplished under exacting government regulated sterile conditions. The completed vials are then placed in the enclosure's bottom half 24, the tubing 62 is positioned within the mating arched openings 26, and the top half 22 is placed over the bottom and attached by snapping into place. The invention is then ready to be utilized.

While the invention has been described in complete detail and pictorially shown in the accompanying drawings, it is not to be limited to such details, since many changes and modifications may be made to the invention without departing from the spirit and scope thereof Hence, it is described to cover any and all modifications and forms which may come within the language and scope of the appended claims.

What is claimed is:

1. A controlled medicament security enclosure system for housing reservoirs comprising:
   a) a portable enclosure of a configuration to accept medicament reservoirs, said enclosure having a top half and a bottom half defined such that they permanently snap together to form a secure, inseparable repository for the reservoirs,
   b) at least one glass medicament vial, defined as a reservoir, disposed within the enclosure having liquid medicament therein,
   c) a sliding piston stopper compressed within the vial contiguously engaging the medicament such that the stopper is free to slide within the vial confines in a hermetically sealed manner when medicament is transferred therefrom, said stopper also having stopper attachment means integrally formed therewith,
   d) an adapter socket having a hollow needle therein, socket attachment means integrally formed therewith and a fluid outlet, said socket attached to the stopper socket attachment means and the needle penetrating the stopper such that the needle is in communication with the medicament and the fluid outlet,
   e) a first tubing connector attached to said adapter socket fluid outlet for interface therewith,
   f) a flexible outlet tube attached to said first tubing connector for transferring medicament from the vial, and
   g) a second outlet tubing connector attached to said flexible outlet tube for interfacing with and delivering medicament to a drug delivery device that includes a pumping and control mechanism.

2. A controlled medicament security enclosure system for housing reservoirs comprising:
   a) a portable enclosure of a configuration to accept medicament reservoirs, said enclosure having a top half and a bottom half defined such that they permanently snap together to form a secure, inseparable repository for the reservoirs, wherein the enclosure's top half and bottom half each having a mating arched opening which jointly creates a round opening for outlet tube egress,
   b) at least one glass medicament vial, defined as a reservoir, disposed within the enclosure having liquid medicament therein, wherein said portable enclosure is configured and is of a size on its interior to accommodate said vial,
   c) a sliding piston stopper compressed within the vial contiguously engaging the medicament such that the stopper is free to slide within the vial confines in a hermetically sealed manner when medicament is transferred therefrom, said stopper also having stopper attachment means integrally formed therewith,
   d) an adapter socket having a hollow needle therein, socket attachment means integrally formed therewith and a fluid outlet, said socket attached to the stopper socket attachment means and the needle penetrating the stopper such that the needle is in communication with the medicament and also the fluid outlet,
   e) a first tubing connector attached to said adapter socket fluid outlet for interface therewith,
   f) a flexible outlet tube attached to said first tubing connector for transferring medicament from the vial, wherein said flexible outlet tube comprises a resilient hollow intravenous tube, wherein the tube free length is longer than the vial length, and g) a second outlet tubing connector attached to said flexible outlet tube for interfacing with and delivering medicament to a drug delivery device that includes a pumping and control mechanism.

3. The controlled medicament security enclosure system as recited in claim 2 further comprising a Y fitting that is attached to the outlet tube when two vials of medicament are employed for connecting the outlet tube from each vial to join the tube into a single outlet.

4. The controlled medicament security enclosure system as recited in claim 2 wherein said portable enclosure is disposable after usage, as the enclosure half's are permanently secured.

5. The controlled medicament security enclosure system as recited in claim 2 wherein said portable enclosure further having a plurality of notched recesses in the top half, and the bottom half having a plurality of mating tapered jaws, or visa versa, such that the jaws are urged outwardly when the half's are pressed together, permitting the jaws to snap into the recesses and forming a non-removable junction.

6. The controlled medicament security enclosure system as recited in claim 2 wherein said hollow needle in said adapter socket is less that 2 inches (5.08 cm) in length.

7. The controlled medicament security enclosure system as recited in claim 2 wherein said portable enclosure is constructed of a thermoplastic material selected from a group consisting of polyethylene, polystyrene, polypropylene, polycarbonate, polyester, polyvinylchloride, polysulfone, polyurethane and cellulose.

8. The controlled medicament security enclosure system as recited in claim 2 wherein said medicament vial is tubular having straight walls, and is closed on a first end and open on a opposed second end.

9. A controlled medicament security enclosure system for housing reservoirs comprising:
a) a portable enclosure of a configuration to accept medicament reservoirs, said enclosure having a top half and a bottom half defined such that they permanently snap together to form a secure, inseparable repository for the reservoirs,
b) at least one glass medicament vial, defined as a reservoir, disposed within the enclosure having liquid medicament therein, wherein said portable enclosure further comprising a partition barrier within the enclosure to separate vials when more than one vial is housed within said enclosure,
c) a sliding piston stopper compressed within the vial contiguously engaging the medicament such that the stopper is free to slide within the vial confines in a hermetically sealed manner when medicament is transferred therefrom, said stopper also having stopper attachment means integrally formed therewith,
d) an adapter socket having a hollow needle therein, socket attachment means integrally formed therewith and a fluid outlet, said socket attached to the stopper socket attachment means and the needle penetrating the stopper such that the needle is in communication with the medicament and also the fluid outlet,
e) a first tubing connector attached to said adapter socket fluid outlet for interface therewith,
f) a flexible outlet tube attached to said first tubing connector for transferring medicament from the vial, wherein said flexible outlet tube comprises a resilient hollow intravenous tube, wherein the tube free length is longer than the vial length, and
g) a second outlet tubing connector attached to said flexible outlet tube for interfacing with and delivering medicament to a drug delivery device that includes a pumping and control mechanism.

10. A controlled medicament security enclosure system for housing reservoirs comprising:
a) a portable enclosure of a configuration to accept medicament reservoirs, said enclosure having a top half and a bottom half defined such that they permanently snap together to form a secure, inseparable repository for the reservoirs,
b) at least one glass medicament vial, defined as a reservoir, disposed within the enclosure having liquid medicament therein,
c) a sliding piston stopper compressed within the vial contiguously engaging the medicament such that the stopper is free to slide within the vial confines in a hermetically sealed manner when medicament is transferred therefrom, said stopper also having stopper attachment means integrally formed therewith, wherein said sliding piston stopper is formed of a resilient material, and the stopper further comprises a plurality of compressible peripheral chevrons for sealing to the vial, said integrally formed stopper attachment means comprise stopper external threads on an end opposite the chevrons,
d) an adapter socket having a hollow needle therein, socket attachment means integrally formed therewith and a fluid outlet, said socket attached to the stopper socket attachment means and the needle penetrating the stopper such that the needle is in communication with the medicament and also the fluid outlet,
e) a first tubing connector attached to said adapter socket fluid outlet for interface therewith,
f) a flexible outlet tube attached to said first tubing connector for transferring medicament from the vial, wherein said flexible outlet tube comprises a resilient hollow intravenous tube, wherein the tube free length is longer than the vial length, and
g) a second outlet tubing connector attached to said flexible outlet tube for interfacing with and delivering medicament to a drug delivery device that includes a pumping and control mechanism.

11. The controlled medicament security enclosure system as recited in claim 10 wherein said integrally-formed, adapter socket attachment means comprise adapter internal threads that interface with said stopper external threads, and said adapter socket further comprises a set of adapter socket outlet internal threads surrounding the fluid outlet, wherein the diameter of the adapter socket is less than the vial internal diameter.

12. The controlled medicament security enclosure system as recited in claim 11 wherein said first tubing connector further having external threads thereon that interface with said adapter socket internal threads for fluid connection therebetween.

13. A controlled medicament security enclosure system for housing reservoirs comprising:
a) a portable enclosure of a configuration to accept medicament reservoirs, said enclosure having a top half and a bottom half defined such that they permanently snap together to form a secure, inseparable repository for the reservoirs,
b) at least one glass medicament vial, defined as a reservoir, disposed within the enclosure having liquid medicament therein,
c) a sliding piston stopper compressed within the vial contiguously engaging the medicament such that the stopper is free to slide within the vial confines in a hermetically sealed manner when medicament is transferred therefrom, said stopper also having stopper attachment means integrally formed therewith, d) an adapter socket having a hollow needle therein, socket attachment means integrally formed therewith and a fluid outlet, said socket attached to the stopper socket attachment means and the needle penetrating the stopper such that the needle is in communication with the medicament and also the fluid outlet, e) a first tubing connector attached to said adapter socket fluid outlet for interface therewith, f) a flexible outlet tube attached to said first tubing connector for transferring medicament from the vial, wherein said flexible outlet tube comprises a resilient hollow intravenous tube, wherein the tube free length is longer than the vial length, and g) a second outlet tubing connector attached to said flexible outlet tube for interfacing with and delivering medicament to a drug delivery device that includes a pumping and control mechanism.

14. The controlled medicament security enclosure system as recited in claim 13 wherein said second outlet tubing connector is known by its registered trademark as a LUER LOCK.

15. A controlled medicament security enclosure system for housing at least one glass medicament vial, with each vial having a sliding piston stopper, an adapter socket with a hollow needle therein, further, said security enclosure system having a tubing connector attached to the adapter socket, a flexible outlet tube attached to the tubing connector and a outlet tubing connector attached to the tubing, wherein the security enclosure system comprising:

a portable enclosure of a configuration to accept medicament having a top half and a bottom half permanently snapped together to produce a secure inseparable repository for medicament reservoirs wherein said portable enclosure is configured and is of a size on its interior to accommodate said vial, and the enclosure's top half and bottom half each having a mating arched opening which jointly creates a round opening for outlet tube egress.

16. The controlled medicament security enclosure system as recited in claim 15 wherein said portable enclosure is disposable after usage as the enclosure half's are permanently secured.

17. The controlled medicament security enclosure system as recited in claim 15 wherein said portable enclosure further having a plurality of notched recesses in the top half and the bottom half having a plurality of mating tapered jaws, or visa versa, such that the jaws are urged outward when the half's are pressed together, thus permitting the jaws to snap into the recesses and forming a non-removable junction.

18. The controlled medicament security enclosure system as recited in claim 15 wherein said portable enclosure further comprising a partition barrier within the enclosure to separate vials when more than one vial is housed within said enclosure.

19. The controlled medicament security enclosure system as recited in claim 15 wherein said portable enclosure is constructed of a thermoplastic material selected from a group consisting of polyethylene, polystyrene, polypropylene, polycarbonate, polyester, polyvinylchloride, polysulfone, polyurethane and cellulose.

20. A controlled security enclosure for housing medicament reservoirs which includes at least one glass medicament vial, each having a sliding piston stopper, an adapter socket with a hollow needle therein, a tubing connector attached to the adapter socket, a flexible outlet tube attached to the tubing connector and a outlet tubing connector attached to the tubing, the security enclosure comprising:

a portable enclosure of a configuration to accept medicament, having a top half and a bottom half permanently snapped together to form a secure retainer, said enclosure is rectangular in shape and of a size to accommodate said vial, said enclosure further having half holes for the egress of the outlet tube, said enclosure is disposable and constructed with male and female interface connections, said enclosure further includes a partition barrier for use with more than one vial, and wherein said enclosure is thermoplastic.

* * * * *